United States Patent
Wheat et al.

(10) Patent No.: US 6,790,361 B2
(45) Date of Patent: Sep. 14, 2004

(54) MOBILE PHASE DILUTION SCHEME FOR ENHANCED CHROMATOGRAPHY

(75) Inventors: Thomas E. Wheat, Hopedale, MA (US); Charles H. Phoebe, Uxbridge, MA (US); Mark K. Baynham, Upton, MA (US); Uwe Dieter Neue, Ashland, MA (US); Raymond P. Fisk, Norton, MA (US); Richard C. Turner, Milford, MA (US)

(73) Assignee: Waters Corporation, Milford, MA (US)

( * ) Notice: Subject to any disclaimer, the term of this patent is extended or adjusted under 35 U.S.C. 154(b) by 0 days.

(21) Appl. No.: 10/414,455

(22) Filed: Apr. 14, 2003

(65) Prior Publication Data

US 2004/0035789 A1 Feb. 26, 2004

Related U.S. Application Data (63) Continuation of application No. 09/990,636, filed on Nov. 21, 2001, now abandoned.
(60) Provisional application No. 60/252,436, filed on Nov. 21, 2000.

(51) Int. Cl.$^7$ .............................................. B01D 15/08
(52) U.S. Cl. ........................ 210/656; 210/659; 210/143; 210/198.2
(58) Field of Search ................................. 210/635, 656, 210/659, 143, 198.2; 436/161

(56) References Cited

U.S. PATENT DOCUMENTS

| | | | |
|---|---|---|---|
| 4,634,680 A | * 1/1987 | Kingsley | 436/178 |
| 4,865,746 A | * 9/1989 | Overfield | 210/656 |
| 4,988,446 A | * 1/1991 | Haberman et al. | 210/656 |
| 5,076,909 A | * 12/1991 | Overfield et al. | 208/177 |
| 5,093,004 A | * 3/1992 | Hotier et al. | 210/659 |
| 5,114,590 A | * 5/1992 | Hotier et al. | 210/659 |
| 5,135,657 A | * 8/1992 | Zavitsanos | 210/656 |
| 6,387,273 B1 | 5/2002 | Abedi | 210/656 |

FOREIGN PATENT DOCUMENTS

| | | | |
|---|---|---|---|
| EP | 444 441 A2 | 9/1991 | 210/656 |
| EP | 602 924 A2 | 6/1994 | 210/656 |

OTHER PUBLICATIONS

Snyder, Introduction to Modern Liquid Chromatography, John Wiley and Sons, Inc., 1979, pp. 291, 292, 298, 641, 642.*

Bidlingmeyer, Practical HPLC Methodology and Applications, John Wiley and Sons Inc. 1993, pp. 239, 240, 241, and 242.*

Bidlingmeyer, Preparative Liquid Chromatography, Elsevier, 1987, pp. 42–43, 37, and 79–80.*

Uwe D. Neue, et al. "Design of Rapid Gradient Methods for the Analysis of Combinatorial Chemistry Libraries and the Preparation of Pure Compounds" *Advances in Chromatography 41*, 93–136 (2001).

Thomas E. Wheat, et al., "Mass–directed AutoPurification: Optimization of Separation and Detection Chemistry" 48$^{th}$ ASMS Conference on Mass Spectrometry and Allied Topics (Jun. 11–15, 2000).

* cited by examiner

*Primary Examiner*—Ernest G. Therkorn
(74) *Attorney, Agent, or Firm*—Peter C. Lauro, Esq.; Edwards & Angell, LLP

(57) ABSTRACT

A method and device for increasing the loading capacity of a chromatography column through dilution of a mobile phase at the head of the column. A strong mobile phase is provided for dissolving a sample. A sample is injected into the strong mobile phase, and subsequently diluted with a weak mobile phase. The resulting sample-containing weak mobile phase is passed through a chromatography column for retention and separation of the components of the sample.

21 Claims, 6 Drawing Sheets

Figure 6
Change in Separation Quality With Increasing Injection Load Using Standard Chromatographic Method 1) Diphenhyrdamine 2) Oxybutynin 3) Terfenadine

Figure 8

Comparison Between Use of Fluid Fitting Device of Figure 3 and Dual Inlet Column Design of Figure 4

MOBILE PHASE DILUTION SCHEME FOR ENHANCED CHROMATOGRAPHY

REFERENCE TO RELATED APPLICATIONS

This application is a continuation application of application Ser. No. 09/990,636 filed on Nov. 21, 2001, now abandoned, which claims priority to U.S. Provisional application No. 60/252,436 filed on Nov. 21, 2000. The contents of all of the aforementioned application(s) are hereby incorporated by reference.

BACKGROUND

In many fields of science, purified compounds are required for testing and analysis protocols. Purification of a compound involves separating out a desired component or components from a mixture that contains additional components or impurities. Chromatography is a method of fractionating a mixture to separate components of the mixture. In liquid chromatography, a sample containing a number of components to be separated is injected into a fluid stream, and directed through a chromatographic column. The column is so designed that it separates the mixture, by differential retention on the column, into its component species. The different species then emerge from the column as distinct bands, separated in time.

A typical high performance liquid chromatography system (HPLC system) is comprised of a pump for delivering fluids (the "mobile phase") at a controlled flow rate and composition, an injector to introduce a sample solution into the flowing mobile phase, a tubular column encasement containing a packing material or sorbent (the "stationary phase"), and a detector to register the presence and amount of the sample components in the mobile phase. When the mobile phase is passed through the stationary phase, each component of the sample will emerge from the column at a different time because different components in the sample will have different affinities for the packing material. The presence of a particular component in the mobile phase exiting the column can be detected by measuring changes in physical or chemical properties of the eluent. By plotting the detector's signal over time, response "peaks" corresponding to the presence of each of the components of the sample can be observed and recorded.

Preparative HPLC is a convenient and easy way of isolating and purifying a quantity of a compound for further studies. Preparative HPLC is not limited by scale. Depending on the specific application, Preparative separations can involve very large columns and sample sizes, resulting in multigram yields, or may be performed using very small columns, resulting in microgram yields. Thus, a common distinction between Preparative and Analytical HPLC is that in Preparative HPLC, the sample is collected after purification, whereas in Analytical HPLC, the sample components are simply detected and quantified.

Typical target requirements for a Preparative separation include high recovery of the sample compound at a purity exceeding 90%, and a rapid, efficient routine. A single instrument is required to isolate and purify between fifty and one hundred samples per day. Therefore, it is highly desirable to purify and separate the largest possible quantity of sample with each run, thereby reducing labor, space, operating expense, run time and associated instrumentation costs.

The combination of Preparative HPLC with a mass spectrometer permits a large number of samples to be processed automatically. An automated separation scheme is guided by mass spectrometer detection. The mass spectrometer is set up to detect the expected molecular weight of the target sample and direct the collection of the purified component that contains this molecular weight.

Other approaches to reduce run time in a Preparative HPLC system include providing rapid gradients during gradient elution, and employing a shorter column with smaller particles in the stationary phase. However, these techniques often compromise the results of the analysis, leading to loss of resolution and a deterioration of peak shape, indicating decreased purity of the separated sample.

In Preparative chromatography, it is also desirable to maximize the quantity of sample to be separated per volume of packing material in the column. Smaller volume columns contain less packing material, which often will have a significant impact on the cost of the column. However, the resolution between response peaks in a chromatographic analysis or "run" depends, in part, on the loading capacity of the column. Chromatography results are limited by the loading capacity of the column, defined as a threshold for the maximum volume and/or mass of sample that may be loaded onto the column without compromising results.

The loading capacity for a column can be exceeded in two ways: volume overload; and mass overload. Volume overload can be defined as the volume of injected sample solution where loss of resolution occurs. Mass overload can be defined as the mass of solute in the sample solution above which loss of resolution occurs.

Loading capacity of a column can be measured by injecting a progressively larger amount of sample. Often times, compounds will elute with multiple peaks having different retention times. A load that exceeds the column capacity is characterized by a deterioration of peak shape and loss of resolution in the resulting separation.

The column can be any chromatographic column, either of conventional or cartridge design. The column can also be composed of two or more columns that are interconnected in some way. An example of such an arrangement would be the use of an easily replaceable guard column connected in series upstream from another column, thereby protecting the main column from premature failure due to fouling.

Neue et al. (*Advances in Chromatography*, 41: 93–136 (2001), the disclosure of which is hereby incorporated herein by reference) describe techniques for optimizing a reversed-phase gradient separation by varying the column length, particle sizes and running conditions for the separation. The article further describes optimized sample loading schemes for providing simplified and automatable preparative gradient elution.

It is desirable to enhance the loading capacity of a column, thereby allowing for the purification and isolation of a larger quantity of a purified sample per chromatographic run. An increased loading capacity for a chromatography column also implies less run time required, and lower cost associated with the isolation of a fixed quantity of sample.

SUMMARY OF THE INVENTION

The present invention relates to liquid chromatography instrumentation and solvent delivery systems, and more particularly to a method and apparatus for increasing the loading capacity of a chromatography column through dilution of a mobile phase at the head of the column.

According to one aspect, the present invention provides an enhanced method of separating a sample in a chromatography system, comprising injecting a sample solution into a strong mobile phase to form a sample-containing strong mobile phase, diluting the sample-containing strong mobile phase with a weak mobile phase upstream from the chromatography column to form a sample-containing weak mobile phase, and passing the sample-containing weak mobile phase through a chromatography column According to another aspect, a chromatography system is provided. The chromatography system comprises a first fluid pump for providing a strong mobile phase at a predetermined flow rate and composition, an injector for injecting a sample solution into the strong mobile phase to form a sample-containing strong mobile phase, a second fluid pump for providing a weak mobile phase to the sample-containing strong mobile phase at a predetermined flow rate and composition to form a sample-containing weak mobile phase, a chromatographic column containing a chromatographic sorbent for separating the sample and a column fitting device for combining the sample-containing strong mobile phase with the weak mobile phase to form the sample-containing weak mobile phase prior to the chromatographic sorbent.

According to another aspect, a column fitting device for a chromatographic column is provided. The column fitting device comprises a first conduit configured to connect with a weak mobile phase flow path, a second conduit configured to connect with a sample-containing strong mobile phase flow path, and a third conduit configured to connect with a chromatographic column. The column fitting device mixes a sample-containing strong mobile phase, comprising a sample and a strong mobile phase, with a weak mobile phase to form a sample-containing weak mobile phase, and passes the sample-containing weak mobile phase to the column.

According to another aspect, a chromatographic column is provided. The column comprises a chromatographic sorbent bed, a common inlet fluid path upstream from the sorbent bed, a first inlet fluid connection port configured to connect with the common inlet fluid path, and a second inlet fluid connection port configured to connect with the common inlet fluid path.

In another aspect, a solvent delivery subsystem for a chromatography system is provided. The subsystem comprises a first pump for providing a strong mobile phase, an injector for injecting a sample into the strong mobile phase to form a sample-containing strong mobile phase, a second pump for providing a weak mobile phase and a column fitting device for mixing the weak mobile phase with the sample-containing strong mobile phase to form a sample-containing weak mobile phase According to another aspect, a packaged column fitting device is provided. The packaged column fitting devices comprises a fluid conduit having a first conduit configured to attach to a weak mobile phase flow path, a second conduit configured to connect with a sample-containing strong mobile phase flow path and a third conduit configured to connect with a chromatographic column. The column fitting device is packaged with instructions for use with an enhanced method of separating a sample in a chromatography system.

According to another aspect, a packaged pump for a chromatography system is provided. The packaged pump is configured to provide a weak mobile phase to a sample-containing strong mobile phase at a predetermined flow rate to dilute the sample-containing strong mobile phase. The pump is packaged with instructions for use with an enhanced method of separating a sample in a chromatography system.

DETAILED DESCRIPTION OF THE INVENTION

An illustrative embodiment of the present invention provides an enhanced chromatographic system and method for separating and purifying a sample. The illustrative embodiment will be described below relative to an implementation in a Preparative HPLC system. Those skilled in the art will appreciate that the present invention may also be implemented on other types of chromatography systems. The illustrative embodiment enhances the loading capacity of a chromatography column through a dilution scheme.

The present invention provides an enhanced chromatography method designed to increase the loading capacity of a chromatography column and enhance the separation of a sample in a Preparative HPLC system. In an illustrative embodiment of the present invention, an at-column dilution scheme is implemented into a chromatography system to dilute a strong mobile phase containing the sample prior to introduction of the sample onto the chromatographic column. This dilution has the effect of increasing the loading capacity of a column, thereby allowing a greater quantity of sample to be separated during a chromatographic run. Alternatively, a shorter column may be used to separated a fixed amount of sample, thereby reducing the run time required to separate the fixed amount of sample.

According to the illustrated embodiment, a sample solution is injected into a strong mobile phase. The sample solution may be comprised of a mixture of compounds dissolved in a relatively small volume of solvent, having good solubility for the sample components. One of ordinary skill in the art will recognize that any suitable solvent may be used, depending on the sample, the solubility of the sample, and other related parameters. A common example of a sample solution would be a mixture of drug compounds dissolved in dimethylsulfoxide (DMSO) or other suitable solvent, such as dimethylformamide (DMF), tetrahydrofuran (THF) and mixtures thereof.

The injection of the sample forms a sample-containing, strong mobile phase that is subsequently diluted at the head of a chromatography column by the addition of a weak mobile phase. The resulting solution, a sample-containing weak mobile phase, is introduced into a chromatography column. The dilution of the sample-containing strong mobile phase at the head of a column has the effect of increasing the loading capacity of the column, thereby allowing a greater quantity of sample to be separated during a chromatographic run.

In chromatography, the mobile phase is a fluid chosen to dissolve the sample solution and carry the sample through the stationary phase of the chromatography system. As used herein, mobile phases are termed "strong" or "weak" in relation to each other. The "strength" (e.g., strong or weak) of a mobile phase refers to the elution strength of the mobile phase and is used to describe the affinity that a sample component will have for either the mobile phase or stationary phase.

The terms "strong mobile phase" and "weak mobile phase" are known in the art. As used herein, a "strong mobile phase" refers to a mobile phase that has a high elution strength and results in little or no retention of the sample on the chromatographic sorbent. A sample dissolved in a "strong" mobile phase will have a greater affinity for the mobile phase than the stationary phase, resulting in little or no retention of the sample on the stationary phase and a shorter elution time.

As used herein, a "weak mobile phase" refers to a mobile phase that has a low elution strength and results in higher amount of retention of the sample on the chromatographic sorbent relative to a strong mobile phase. Contrary to a sample dissolved in a strong mobile phase, a sample dissolved in a "weak" mobile phase will have less affinity for the mobile phase than the stationary phase, resulting in sample components being strongly retained on the stationary phase and a longer elution time.

In order for the sorbent bed to preferentially retain sample components, the mobile phase is, at least initially, advantageously of low to intermediate strength. Otherwise the sample components will simply pass through the column with little or no retention or separation. In Gradient Preparative HPLC, the initial mobile phase strength is kept quite low, so that sample components are highly retained on the sorbent bed. The mobile phase strength is then systematically increased over time to elute in turn each sample component. This approach places a solubility limit on the volume and/or mass of sample solution which can be injected into the HPLC.

Depending on the retention mechanism being used, many different mobile phase properties can be used to adjust mobile phase strength. In particular, the solvents are selected so as to adjust the strength of the mobile phase. The types of solvents used are well known to those skilled in the art. For example, in both "Reversed Phase" and "Normal Phase" chromatography, the ratio of organic solvent to water in the mobile phase is typically modified to adjust the strength of the mobile phase. In the case of an ion-exchange-based separation, mobile phase pH and/or ionic strength is commonly manipulated to adjust the strength of the mobile phase. One skilled in the art will recognize that although the examples provided in the present invention focus on "Reversed Phase" separations, the enhanced technique of the present invention can be adapted to other separation modes as well.

In Reversed Phase Chromatography, a non-polar stationary phase is used in conjunction with more polar, largely aqueous mobile phases. Because sample retention in this case is driven by hydrophobic interaction, a strong mobile phase, i.e., one which can easily elute the sample from the stationary phase, will be one having a high percentage of organic solvent. Conversely, a weak mobile phase will have a lower percentage of organic solvent in Reversed Phase Chromatography.

In Normal-Phase Chromatography, the stationary phase is more polar than the mobile phase. A common application of Normal-Phase Chromatography is seen in the use of a polar stationary phase, such as silica or alumina, with a mobile phase having a high percentage of organic solvent. In Normal-Phase, a weak mobile phase would have a high percentage of organic solvent, while a strong mobile phase would have a lower percentage of organic solvent.

In Ion-Exchange Chromatography, retention of the sample on the stationary phase is controlled through the interaction of charged analytes with oppositely charged functional groups on the stationary phase surface. Because both the sample components and the stationary phase could contain either cation or anion exchange groups (and possibly both) these separations are strongly influenced by changes in mobile phase pH and/or ionic strength. In the case of ion-exchange separations, raising or lowering the pH and/or ionic strength of the mobile phase results in either an increase or a decrease in the elution strength of the mobile phase, depending on the pKa of the sample and whether the stationary phase is a cation or anion exchanger. The pH and/or the ionic strength may be raised or lowered as the separation requires, thereby adjusting the elution strength of the mobile phase. A large application area is the separation of biopolymers, specifically proteins and peptides.

Changes in the temperature of the mobile phase can also influence sample retention in many modes of chromatography. Generally, as the temperature of a mobile phase is increased, the mobile phase strength is also increased, resulting in shorter retention time on the stationary phase. Although the effect is not often as dramatic as seen with changes in percentage of organic solvent or pH, it can generally be observed across all modes of chromatography. This effect can be a result of simply increasing the solvating power of a mobile phase at elevated temperature, or of temperature-induced changes to the molecular structure of the sample molecules in solution. A common application area is the separation of samples having complex structure, such as proteins and related biopolymers.

In accordance with the present invention, a strong mobile phase dissolves the sample. The strong mobile phase comprises a strong organic solvent, such as, e.g., 100% acetonitrile, in which the sample has good solubility. A strong mobile is capable of dissolving a larger quantity of a sample than a weak mobile phase. As used herein, the term "sample-containing strong mobile phase" consists of the strong mobile phase and the dissolved sample carried in the strong mobile phase.

Although a strong mobile phase is suitable for dissolving a large quantity of a sample, the strength of this mobile phase causes the sample components to be poorly retained by the sorbent bed, leading to peak distortion and degraded chromatographic separation. To regulate the strength of the solvent prior to passing the sample-containing strong mobile phase through the column, the sample-containing strong mobile phase is diluted by adding a weak mobile phase to the sample-containing strong mobile phase to form a sample-containing weak mobile phase. The "sample-containing weak mobile phase" includes the strong mobile phase, the sample and the weak mobile phase (i.e., the diluent). The sample-containing weak mobile phase is weaker in elution strength than the strong mobile phase, in that the sample has lower affinity for the mobile phase and therefore a higher affinity for the stationary phase. The diluted sample-containing mobile phase is suitable for carrying the sample onto the stationary phase without degrading the chromatographic results.

The above-described technique is capable of significantly increasing the loading capacity of a column. This technique enhances conditions for both dissolving a sample and carrying the sample through a chromatography column. In this manner, a larger quantity of sample may be analyzed in a single chromatography run. A chromatography system devoid of the described dilution scheme is limited to a smaller amount of sample that may be separated without degrading the end result. Application of the enhanced method of separating a sample using the above-described dilution scheme can increase the loading capacity of a column. Preferably, the loading capacity of the column is increased by at least about two-fold, and more preferably between about two-fold and about 80-fold, and still more preferably by at least five-fold; ten-fold; 20-fold; 30-fold; 40-fold; 50-fold; 60-fold; 70-fold; and 80-fold.

In addition to increasing the loading capacity of a column, the enhanced chromatography method results in improvement in peak shape and resolution for a fixed quantity of sample. When a sample is injected into a solvent in which the sample has insufficient solubility, sample precipitation results. This causes troublesome blocking inside injection ports, valves and interconnecting tubing lines. However, a solvent with high sample solubility also leads to poor results, as it tends to carry the sample too far down the length of the column, resulting in unwanted peak broadening and poor separation efficiency. The chromatography method of the present invention reduces precipitation of the sample in injection ports, valves, and interconnecting tubing lines, while also allowing a strong retention of the sample at the head of the chromatography column to improve separation of the different components. By initially providing a strong mobile phase to fully dissolve the sample, and subsequently diluting the mobile phase before introduction onto the column, separation and purification of a sample are enhanced.

Figure 1:
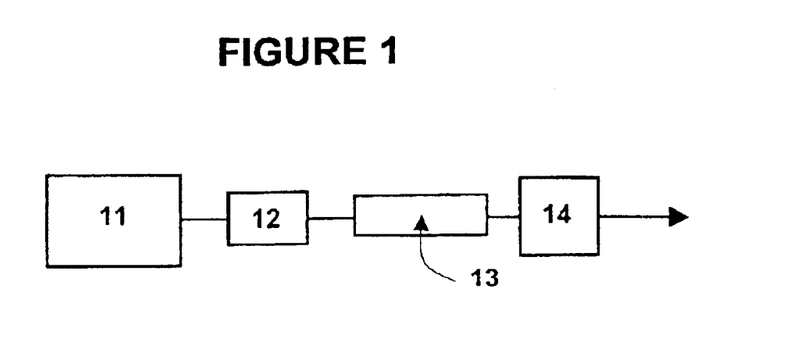
FIG. 1 is an illustration of a traditional instrument configuration for a solvent delivery system in a Preparative chromatography system.

In a traditional Preparative HPLC system, illustrated in FIG. 1, a single gradient pump 11 delivers a variable strength mobile phase of controlled composition to the system. The sample solution to be separated is inserted through an injector loop 12 into the stream of solvent, and delivered to the chromatography column 13 as a slug of sample solution sandwiched in the stream of mobile phase. The mobile phase is forced through the column 13 and passed to a detector 14 for evaluation. Individual sample components are retained to varying degrees on the sorbent bed, and elute in turn from the column over the course of the chromatographic run.

In a Gradient Preparative HPLC the mobile phase solvent strength is varied over the course of the run, in order to achieve the desired separation. An initial low strength mobile phase flowing through the column causes the sample components to be strongly absorbed on the sorbent within the column. After the sample is loaded on the column 13, a gradient is initiated to increase the strength of the mobile phase. The gradient, effected by the gradient pump 11, causes the individual components of the sample to be sequentially eluted from the column 13.

Other separation conditions may require that the mobile phase composition remain fixed over time (this mode being termed "Isocratic Preparative HPLC"). In this case, the mobile phase strength remains fixed at an intermediate level where all of the sample components are partially retained by the sorbent.

There are inherent limitations to the traditional Preparative HPLC system illustrated in FIG. 1. It is desirable to maximize the amount of compound that may be purified and isolated in a chromatography run. An initial approach would be to load an increased volume of a sample solution, comprised of a sample dissolved in a suitable solvent. However, it has been found that a large volume of sample solution, when injected into the system, degrades chromatography and creates peak distortions due to volume overload. Therefore, it would be desirable to load the largest amount of compound in a small volume of solution to limit the total injection volume. This results in a high sample concentration. High sample concentrations require a strong solvent. However, the strong solvent also degrades the separation and creates peak distortions due to mass overload. Therefore, solubility of a sample in the mobile phase of the system illustrated in FIG. 1 is limited. These conflicting principles must be resolved in order to provide optimal separation of a large amount of compound in a chromatography system, without excessive mass or excessive volume overload.

Figure 2:
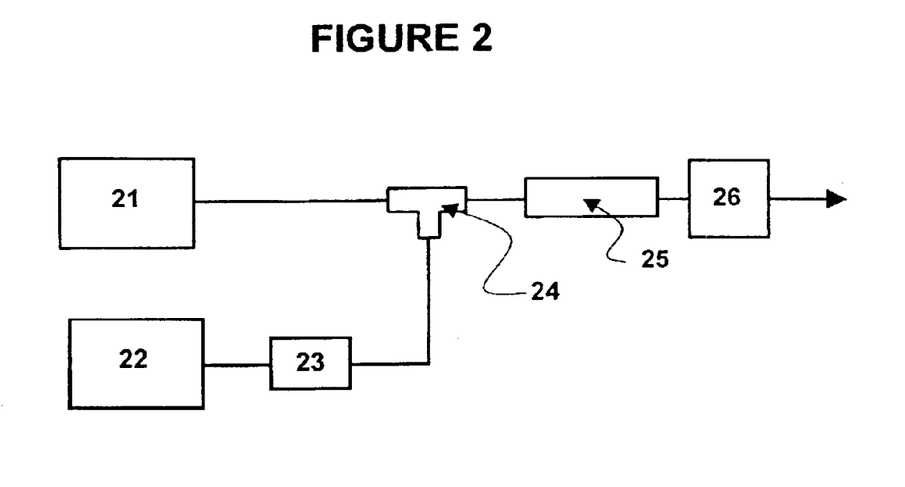
FIG. 2 is an illustration of an instrument configuration for a solvent delivery system in a Preparative chromatography system according to the teachings of the present invention, utilizing a single solvent loading pump together with a multisolvent gradient delivery pump.

The present invention overcomes these limitations by increasing the apparent loading capacity of a column to maximize the amount of sample that can be separated per run cycle. Thus, the present invention, as illustrated in FIG. 2, provides a chromatographic column 25 for separating a sample, a loading pump 22 for providing a strong mobile phase, such as, e.g., acetonitrile, to the system and a separate gradient pump 21 for providing a variable strength, weak mobile phase flow to the system and a fitting 24 in communication with the column 25 for combining the outputs of the loading pump 22 and the gradient pump 21. The loading pump 22 delivers a stream of a strong mobile phase through the injector 23. A sample is first dissolved in a solvent and then injected through the injector 23 into the strong mobile phase stream to form a sample-containing strong mobile phase. In this case, a high concentration of sample in a small volume of solution is permitted. The sample is carried to the fitting 24 as a slug sandwiched in the strong mobile phase stream. At the fitting 24, the sample-containing strong mobile phase, comprised of the sample solution and high strength mobile phase, is diluted with a weak mobile phase flow from the gradient pump 21 to form a sample-containing weak mobile phase. The sample-containing weak mobile phase is then passed through the fitting 24 to the column 25. The diluted, sample-containing weak mobile phase, comprised of the sample solution and the combination of the mobile phases from the gradient pump and the loading pump, is passed through the column 25 and subsequently conveyed to detectors 26 for evaluation and collection of the purified compound.

In a preferred embodiment, the initial flow rate of the weak mobile phase from the gradient pump 21 is greater than the initial flow rate of the strong mobile phase; advantageously, the initial flow rate of the weak mobile phase is at least about twenty times the initial flow rate of the strong mobile phase from the loading pump 22. In this manner, the diluted mobile phase at the head of the column contains 5% of the strong mobile phase and 95% of the weak mobile phase, which is similar to the mobile phase at the head of the column in the system of FIG. 1 at the start of a gradient separation.

In an alternate embodiment of the present invention, two single solvent, or non-gradient pumps can be used, where one pump delivers only the strong mobile phase flow, and a second pump delivers only the weak mobile phase flow. The system is identical to the system shown in FIG. 2, with the exception that the gradient pump 21 is replaced with a single solvent isocratic pump that delivers a weak mobile phase of fixed composition. In this embodiment, the mobile phase composition entering the column is controlled by flow programming of the two single solvent pumps. A potential advantage of this embodiment may be in lower instrumentation cost associated with the gradient pump 21.

Figure 3:
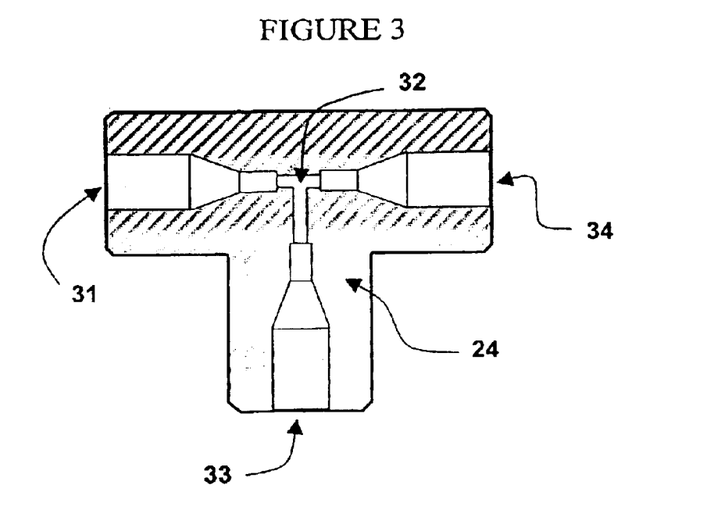
FIG. 3 is an illustration of a column fitting used in accordance with the teachings of the present invention to increase the loading capacity of a chromatographic column.

A suitable fitting 24 used for the above-described mobile phase dilution scheme is illustrated in FIG. 3. The fitting 24 is comprised of three fluid conduits having a common flow path. A flow path 31 delivers the sample-containing strong mobile phase to a junction point 32. A dilution flow path 33 delivers the weak mobile phase to the junction point 32. At the junction point 32, the sample-containing strong mobile phase is combined and diluted with the weak mobile phase to form a sample-containing weak mobile phase. This sample-containing weak mobile phase passes through the third conduit 34 and onto the head of the column (25 in FIG. 2).

The junction point 32 may comprise a cavity having any suitable size and shape for mixing the two flow paths. The junction point 32 may further include a mixing element to facilitate dilution and mixing of a sample-containing strong mobile phase with a weak mobile phase.

According to the embodiment shown in FIG. 3, the fitting 24 is interposed between a chromatography column, a gradient pump and a loading pump. The fitting may be connected to the inlet of the chromatographic column and the outlets of the gradient pump and the loading pump through any suitable means known in the art. For example, one or more of the ends of the conduits 31, 33 or 34 may be threaded to facilitate connection with the loading pump, the chromatographic column and/or the gradient pump, respectively. Alternatively, the conduits may be connected to the inlet of the chromatography column and/or the outlets of the gradient pump and the loading pump by friction-fit. The conduits 31, 33, 34 forming the fitting 24 may have any suitable size, and shape, depending on the particular application.

Figure 4:
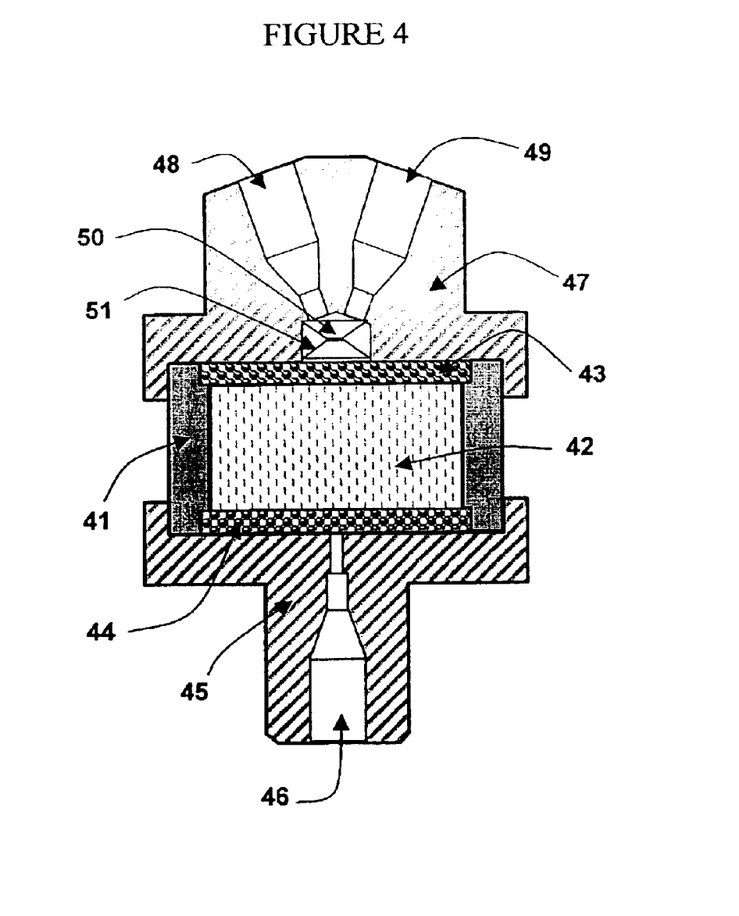
FIG. 4 is a detailed drawing of a chromatographic column with multiple inlet ports for providing at column dilution of a mobile phase according to the teachings of the invention.

An alternate design for the column fitting is illustrated in FIG. 4. In FIG. 4, the column fitting for combining two flow paths and delivering the combined flow path to a column is integrally formed on a chromatographic column 40. The column body 41 is a tube of various length, diameter, and material chosen for the intended use and is packed with a chromatographic sorbent 42 which may be of various particle size, shape, or chemical composition. The bed is contained at both inlet and outlet ends by porous filter elements 43, 44, that have been chosen to retain the stationary phase. The filter elements may be sealed in place using a number of techniques, including press fitting into either the column end fitting or column body. A column outlet end fitting 45 attaches the outlet filter 44 to the column body 41, and includes a fluid connection port 46 for the fluid exiting the column. A column inlet end fitting 47 attaches the inlet filter 43 to the column body 41, and provides multiple connection ports 48, 49 for fluid streams entering the column. In a preferred embodiment, the first connection port 48 delivers a sample-containing strong mobile phase to the column and the second connection port 49 delivers a weak mobile phase to the column. The fluid streams are then mixed in close proximity to the chromatographic bed 42 to dilute the sample-containing strong mobile phase.

In an alternate design, the fluid streams entering the column are combined in a recessed cavity 50 located within the inlet end fitting, where they are acted on by a mixing element 51, which is inserted into the cavity 50. The mixing element may be of any conventional design. Once mixed, the diluted sample-containing mobile phase passes through the inlet filter and the chromatographic bed, and then eventually exits the column. In a preferred embodiment, the column can be of a cartridge system design, consisting of a cartridge holder, which includes the previously described fluid connection ports, and mixing elements, and a removable cartridge type column, which contains the packed chromatographic sorbent bed and retaining porous filter elements.

Figure 5:
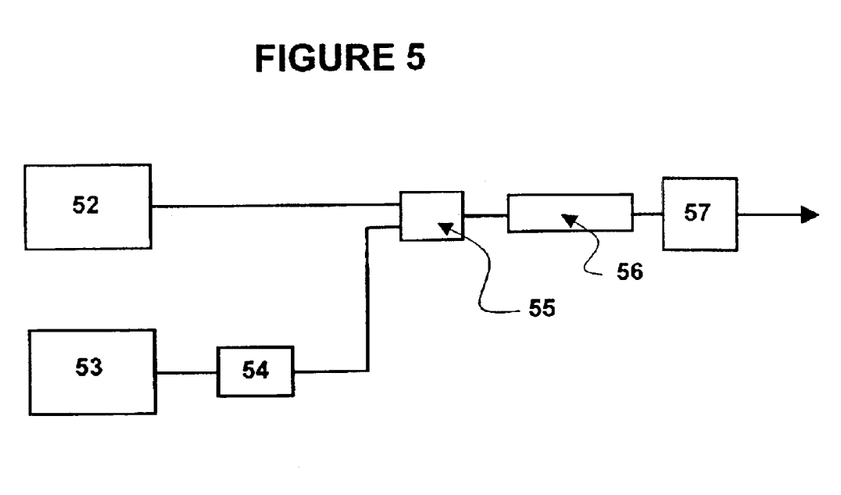
FIG. 5 is an illustration of an alternate instrument configuration for a solvent delivery system in a Preparative chromatography system according to the teachings of the present invention, where the chromatographic column is comprised of a guard column with multiple inlet ports connected in series with another chromatographic column.

An embodiment of the complete Preparative system of an illustrative embodiment of the present invention is illustrated in FIG. 5. A loading pump 53 provides a controlled flow of strong mobile phase through an injector 54 and into the head of a multiple inlet guard column 55 through a first inlet. A gradient pump 52 provides a controlled flow of variable strength, weak mobile phase to a second inlet of the guard column 55. The fluids entering the column 55 are mixed in close proximity to the sorbent bed and are passed onto the chromatographic sorbent contained within columns 55 and 56 for separation and eventual detection by a detector 57.

The dilution scheme of the present invention enhances chromatographic results significantly. A strong initial mobile phase for dissolving a sample permits loading of a large amount of a sample in a small volume. This maximizes dissolution of the sample in the mobile phase. By subsequently diluting the sample-containing strong mobile phase prior to introduction of the sample onto the column, optimum separation conditions are achieved. The illustrative dilution scheme resolves the conflicting principles of both a large injection volume and a strong sample solvent degrading chromatography.

An enhanced loading capacity provides significant advantages for reducing the time required to purify and isolate a quantity of compound, and therefore the operating costs, of a separation. For a given sample size, a shorter column may be used, leading to a reduced run time, lower solvent consumption, and reduced column expense while producing high-quality results. Therefore, an increased number of samples, may be purified on a single chromatography system per day. For a given column size, a larger load of sample can be purified during each run, thereby decreasing the number of runs required to purify a specific quantity of sample.

In addition, the implementation of the dilution scheme of the present invention provides increased resolution, and improved peak shape for a given mass of sample, thereby enhancing the purity of collected peaks These effects are illustrated in the non-limiting examples below.

EXEMPLIFICATION OF THE INVENTION

Example 1

The Change in Separation Quality with Increasing Injection Load Using a Standard Chromatographic Method

A sample mixture is prepared by combining Diphenhydramine, Oxybutynin, and Terfenadine, at a concentration of 20 milligrams per milliliter for each component, using dimethylsulfoxide (DMSO) as the sample solvent. A standard chromatographic system as described in FIG. 1 is used to separate the sample, where the column 13 is comprised of a 19 mm internal diameter×10 mm long guard column of conventional design connected in series with a 19 mm internal diameter×30 mm long column of conventional design. The chromatographic columns are packed with standard reversed phase C18 bonded sorbent (Waters' XTerra MS-C 18, 5 micron particles). A linear gradient elution profile is used, with a starting mobile phase composition of 5% acetonitrile/95% water containing ammonium bicarbonate pH 10 buffer, and a final mobile phase composition of 90% acetonitrile/10% water containing ammonium bicarbonate pH 10 buffer. The mobile phase composition profile versus time is set forth in Table 1 below. Flow rate is set to 30 milliliters per minute, and a UV detector of conventional design is used to monitor the column effluent.

Figure 6:
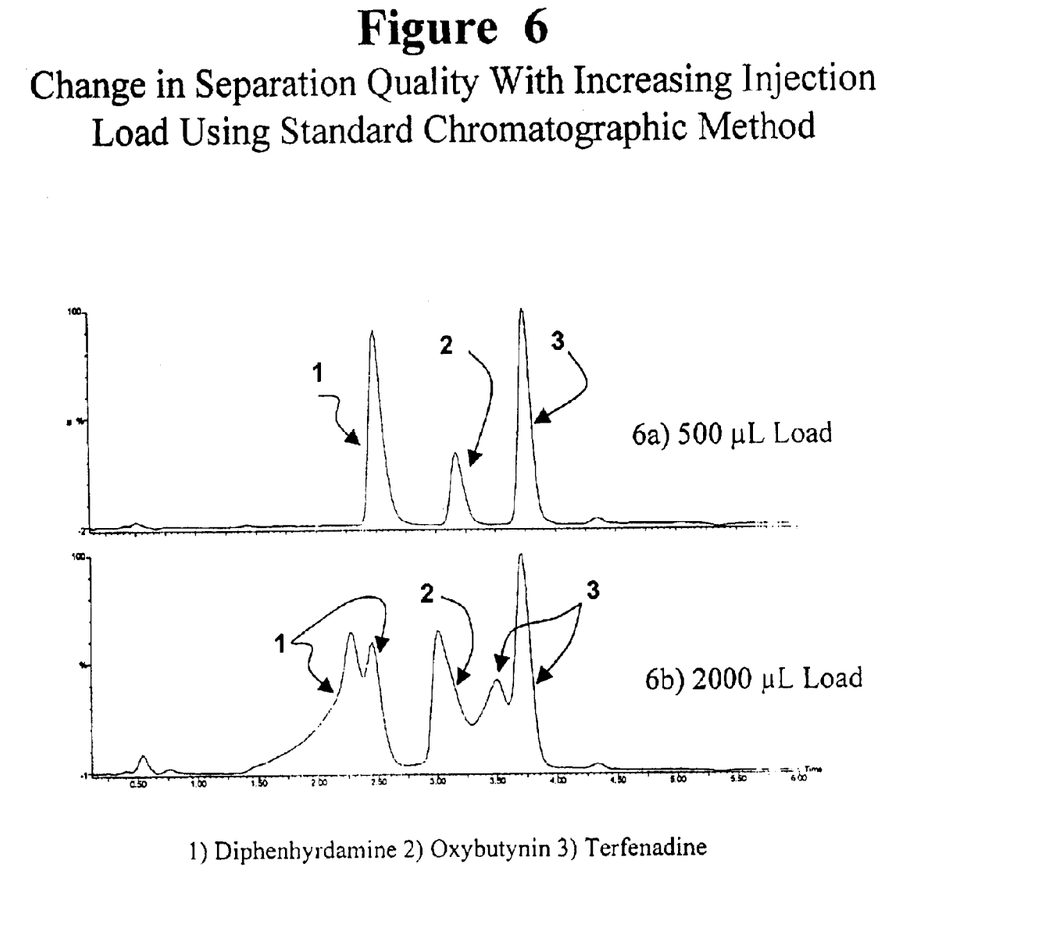
FIG. 6a is a chromatogram illustrating a separation of a 500-$\mu$L-sample solution for a standard chromatography system.
FIG. 6b is a chromatogram illustrating a separation of a 2000 $\mu$L sample solution for a standard chromatography system.

FIGS. 6a and 6b show separation results for 500 μL and 2000 μL sample injection volumes, respectively, using the standard chromatography system of FIG. 1. As the injection load increases from 500 μL to 2000 μL, the baseline resolution between peaks is no longer achieved, and peaks 1 and 3 split to form multiple peaks. The loss of resolution and the appearance of split peaks in FIG. 6b result from exceeding the loading capacity of the chromatographic column.

TABLE 1

| Time | Water | Acetonitrile | 100 mM NH$_4$HCO$_3$, pH10 |
|---|---|---|---|
| Standard System As Used In Example 1 | | | |
| 0.00 | 90 | 5 | 5 |
| 0.50 | 90 | 5 | 5 |
| 0.60 | 55 | 40 | 5 |
| 4.00 | 5 | 90 | 5 |
| 4.30 | 5 | 90 | 5 |
| 4.40 | 90 | 5 | 5 |
| 6.00 | 90 | 5 | 5 |
| At-Column Dilution System As Used In Example 2 and 3 | | | |
| 0.00 | 90 | 5 | 5 |
| 2.50 | 90 | 5 | 5 |
| 2.60 | 55 | 40 | 5 |
| 6.00 | 5 | 90 | 5 |
| 6.30 | 5 | 90 | 5 |
| 6.40 | 90 | 5 | 5 |
| 8.00 | 90 | 5 | 5 |

Example 2

The Change in Separation Quality with Increasing Injection Load Using the Enhanced Chromatographic Method of the Illustrative Embodiment of the Present Invention

A chromatographic system is used as shown in FIG. 2, where the column 25, and detector 26 are identical to those described in Example 1. A fitting device 24 (as shown in FIG. 3) is placed in front of column 25. A linear gradient elution profile is delivered from gradient pump 21 at a flow rate of 28.5 milliliters per minute. The loading pump 22 is set to a flow rate of 1.5 milliliters per minute, resulting in a total combined flow rate of 30 milliliters per minute, similar to the first Example. The gradient composition over time is set forth above in Table 1. The same gradient composition is used as in Example 1, however, an initial hold is added to the gradient to allow pumping of the loading solvent from the loading pump 22 through the injector 23, thereby ensuring that the sample is completely transferred to the column before the gradient starts. The same sample mixture is injected onto the system as used in Example 1.

Figure 7:
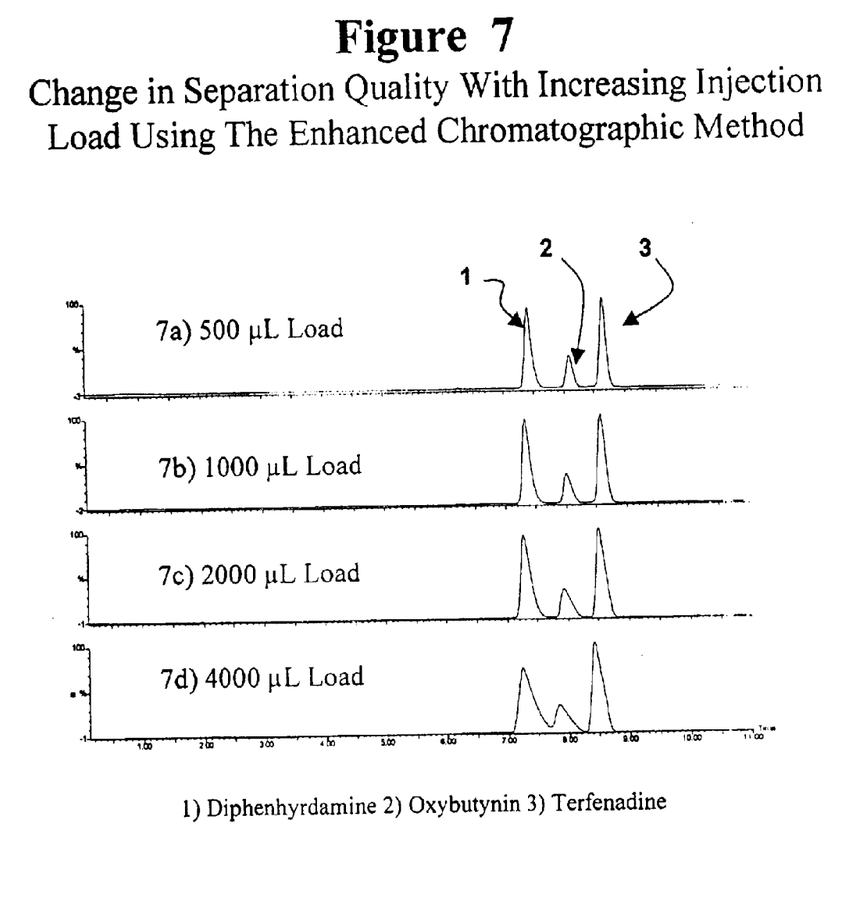
FIG. 7a is a chromatograph illustrating a separation of a 500 $\mu$L sample solution using the chromatography system of FIG. 2.
FIG. 7b is a chromatogram illustrating a separation of a 1000 $\mu$L sample solution using the chromatography system of FIG. 2.
FIG. 7c is a chromatogram illustrating a separation of a 2000 $\mu$L sample solution using the chromatography system of FIG. 2.
FIG. 7d is a chromatogram illustrating a separation of a 4000 $\mu$L sample solution using the chromatography system of FIG. 2.

FIGS. 7a, b, c, & d show separation results for 500, 1000, 2000, and 4000 μL sample injection volumes, respectively. As the injection load increases, it can be seen that the baseline resolution between peaks is maintained, with excellent baseline resolution and no occurrence of split peaks. As shown, the use of the column fitting device to dilute the sample-containing strong mobile phase prior to introduction to the column significantly increases the loading capacity of the volume, when compared with a standard chromatography system that does not use the dilution scheme, as described in Example 1.

Example 3

A Comparison Between the Use of the Embodiment of FIG. 3 and the Embodiment of FIG. 4

A chromatographic system is arranged as shown in FIG. 5. The configuration of FIG. 5 is identical to that used in Example 2, with the exception that the guard column 55 contains an integral dual inlet design (as shown in FIG. 4) to provide the mobile phase dilution scheme of the illustrative embodiment. The integral dual inlet design is used in place of the fitting device 24 in Example 2. The sample composition, gradient elution profile, and all mobile phase flow rates are identical to those used in Example 2.

Figure 8:
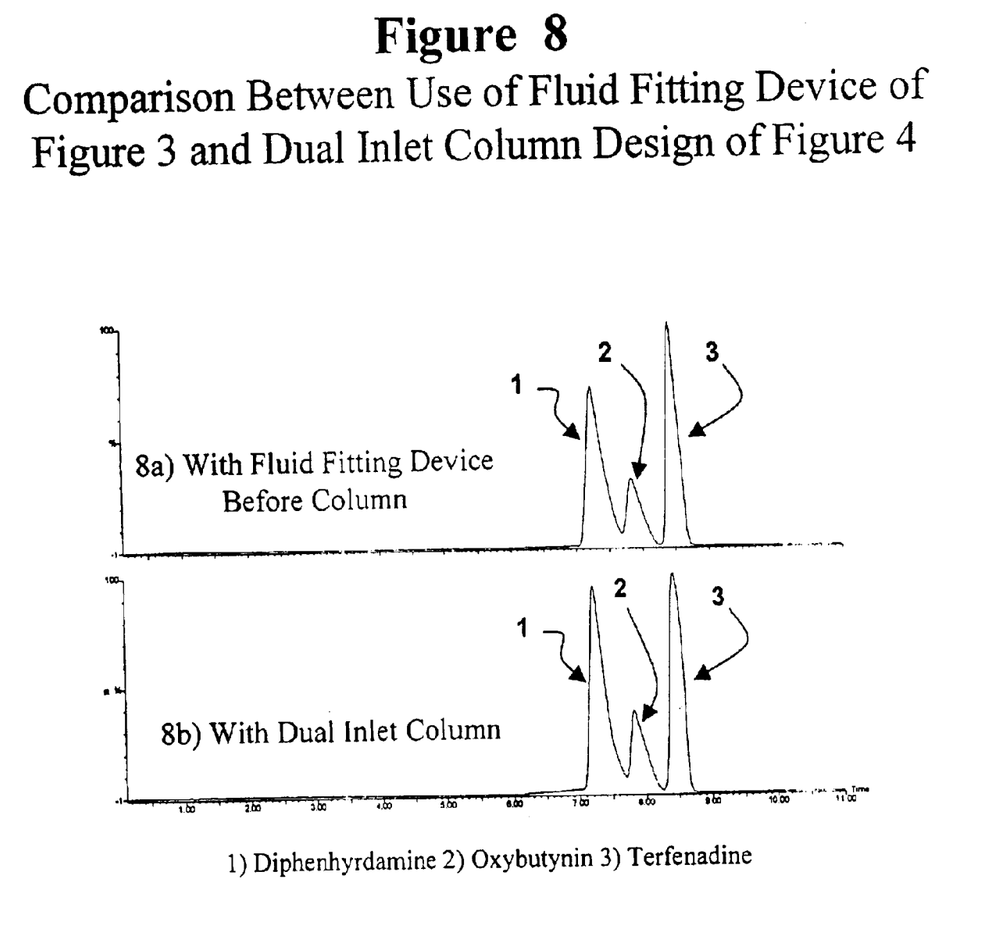
FIG. 8a is a chromatogram illustrating a separation using the column fitting device and column of FIG. 3.
FIG. 8b is a chromatogram illustrating a separation using a column having multiple inlet ports as illustrated in FIG. 5.

FIG. 8a and b compares separation results for a 4000 μL injection of sample solution using the chromatographic methods and systems described in Examples 2 and 3, respectively. The results show that the column having an integral multiple inlet design, as set forth in Example 3, performs in a substantially similar manner to the chromatographic fitting device of Example 2.

Although the invention has been described in detail with reference to an illustrative embodiment and application, those skilled in the art will appreciate that various modifications and variations may be made without departing from the intended scope of the present invention as defined in the appended claims.

Having described the invention, what is claimed as new and desired to be secured by Letters Patent is:

1. An enhanced chromatographic method of separating a sample in a chromatography system, comprising:
   injecting a sample solution into a strong mobile phase to form a sample-containing strong mobile phase,
   diluting the sample-containing strong mobile phase to form a sample-containing weak mobile phase, and
   passing the sample-containing weak mobile phase through a chromatography column, wherein the pH of the sample-containing weak mobile phase is different from the pH of the sample-containing strong mobile phase, thereby providing an enhanced chromatographic method.

2. The enhanced chromatographic method of claim 1, wherein the enhanced chromatographic method increases the loading capacity of the column.

3. The enhanced chromatographic method of claim 2, wherein the enhanced chromatographic method increases the loading capacity of the column by at least two-fold.

4. The enhanced method of claim 2, wherein the enhanced chromatographic method increases the loading capacity of the column by at least five-fold.

5. The enhanced method of claim 2 wherein the enhanced chromatographic method increases the loading capacity of the column by at least ten-fold.

6. The enhanced method of claim 2, wherein the enhanced chromatographic method increases the loading capacity of the column by at least twenty-fold.

7. The enhanced method of claim 2 wherein the enhanced chromatographic method increases the loading capacity of the column by at least thirty-fold.

8. The enhanced method of claim 2, wherein the enhanced chromatographic method increases the loading capacity of the column by at least sixty-fold.

9. The enhanced method of claim 2, wherein the enhanced chromatographic method increases the loading capacity of the column by at least eighty-fold.

10. The enhanced method of claim 1, wherein the percentage of organic solvent in the sample-containing weak mobile phase is different from the percentage of organic solvent in the sample-containing strong mobile phase.

11. The enhanced method of claim 10, wherein the percentage of organic solvent in the sample-containing weak mobile phase is less than the percentage of organic solvent in the sample-containing strong mobile phase.

12. The enhanced method of claim 10, wherein the percentage of organic solvent in the sample-containing weak mobile phase is greater than the percentage of organic solvent in the sample-containing strong mobile phase.

13. The enhanced method of claim 1, wherein the pH of the sample-containing weak mobile phase is less than the pH of the sample-containing strong mobile phase.

14. The enhanced method of claim 1, wherein the pH of the sample-containing weak mobile phase is greater than the pH of the sample-containing strong mobile phase.

15. The enhanced method of claim 1, wherein the ionic strength of the sample-containing weak mobile phase is different from the ionic strength of the sample-containing strong mobile phase.

16. The enhanced method of claim 15, wherein the ionic strength of the sample-containing weak mobile phase is less than the ionic strength of the sample-containing strong mobile phase.

17. The enhanced method of claim 15, wherein the ionic strength of the sample-containing weak mobile phase is greater than the ionic strength of the sample-containing strong mobile phase.

18. The enhanced method of claim 1, wherein the temperature of the sample-containing weak mobile phase is different from the temperature of the sample-containing strong mobile phase.

19. The enhanced method of claim 18, wherein the temperature of the sample-containing weak mobile phase is less than the temperature of the sample-containing strong mobile phase.

20. The enhanced method of claim 1, wherein the strong and weak mobile phases each have an initial flow rate, and wherein the initial flow rate of the weak mobile phase is greater than the initial flow rate of the strong mobile phase.

21. The enhanced method of claim 20, wherein the initial flow rate of the weak mobile phase is at least 20 times greater than the initial flow rate of the strong mobile phase.

* * * * *